United States Patent [19]

Gratton et al.

[11] Patent Number: 5,497,769
[45] Date of Patent: Mar. 12, 1996

[54] PHOTOSENSOR WITH MULTIPLE LIGHT SOURCES

[75] Inventors: Enrico Gratton; Sergio Fantini; Maria A. Franceschini, all of Urbana; William Mantulin; Beniamino Barbieri, both of Champaign, all of Ill.

[73] Assignees: I.S.S. (USA) Inc.; The Board of Trustees of the University of Illinois, both of Champaign, Ill.

[21] Appl. No.: 168,813

[22] Filed: Dec. 16, 1993

[51] Int. Cl.$^6$ .................................................. A61B 5/00
[52] U.S. Cl. ......................... 128/633; 128/664; 128/666; 356/41
[58] Field of Search ..................... 128/633–634, 128/664–666; 356/35–41

[56] References Cited

U.S. PATENT DOCUMENTS

| | | |
|---|---|---|
| 4,840,485 | 6/1989 | Gratton . |
| 4,854,699 | 8/1989 | Edgar, Jr. .................. 128/633 |
| 4,972,331 | 11/1990 | Chance . |
| 5,032,024 | 7/1991 | Cope . |
| 5,057,695 | 10/1991 | Hirao et al. ............... 356/41 |
| 5,122,974 | 6/1992 | Chance . |
| 5,167,230 | 12/1992 | Chance . |
| 5,187,672 | 2/1993 | Chance et al. . |
| 5,188,108 | 2/1993 | Secker ....................... 128/633 |
| 5,209,231 | 5/1993 | Cote et al. . |
| 5,212,386 | 5/1993 | Gratton et al. . |
| 5,213,105 | 5/1993 | Gratton et al. . |
| 5,243,983 | 9/1993 | Tarr et al. . |
| 5,267,152 | 11/1993 | Yang et al. . |
| 5,331,958 | 7/1994 | Oppenheimer . |
| 5,348,003 | 9/1994 | Caro ........................... 128/665 |

FOREIGN PATENT DOCUMENTS

| | | |
|---|---|---|
| 2228314 | 2/1989 | United Kingdom . |
| 04970211 | 8/1992 | United Kingdom . |
| WO90/09003 | 8/1989 | WIPO . |

OTHER PUBLICATIONS

Patterson et al. article by Applied Optics, vol. 30, No. 31, pp. 4474–4476—Nov. 1, 1991.
Patterson et al. article by Applied Optics, vol. 28, No. 12 pp. 2331–2336—Jun. 15, 1989.
Article by J. R. Lakowicz et al. entitled: Frequency–Domain Fluorescence Spectroscopy, a New Method for the Resolution of Complex Fluorescence Emission from Trends in Analytical Chemistry, Nov., 1986, pp. 257–263.
Article entitled: "Time–Resolved Spectroscopy of the Human Forearm" by Ferrari et al.—J. Photochem. Photobiol. B: Biol., 16 (1992) 141–153.
Article entitled: "Tissue Characterization and Imaging Using Photon Density Waves" by Svaasand et al.—Optical Engineering, Feb., 1993, vol. 32 No. 2, pp. 258–265.

*Primary Examiner*—Angela D. Sykes
*Assistant Examiner*—Robert L. Nasser, Jr.
*Attorney, Agent, or Firm*—Gerstman, Ellis McMillin, Ltd.

[57] ABSTRACT

The quantitative determination of various materials in highly scattering media such as living tissue may be determined in an external, photometric manner by the use of a plurality of light sources positioned at differing distances from a sensor. The light from said sources is amplitude modulated, and, in accordance with conventional frequency domain fluorometry or phosphorimetry techniques, the gain of the sensor is modulated at a frequency different from the frequency of the light modulation. Data may be acquired from each of the light sources at differing distances at a frequency which is the difference between the two frequencies described above. From these sets of data from each individual light source, curves may be constructed, and the slopes used to quantitatively determine the amount of certain materials present, for example oxyhemoglobin and deoxyhemoglobin in living tissue.

27 Claims, 3 Drawing Sheets

PHOTOSENSOR WITH MULTIPLE LIGHT SOURCES

BACKGROUND OF THE INVENTION

The determination of the optical properties of tissues is of fundamental importance in many fields of medicine, both for diagnostic and monitoring purposes. It is well known that light of differing wavelengths penetrates differently in various tissues. In the near infrared region, for example, (about 650 nm to about 1000 nm), light of this wavelength penetrates several centimeters through tissue. It is intended that the term "light" includes other electromagnetic radiation as well which is invisible to the human eye, for example, infrared and ultraviolet.

Because of the capability of various forms of light to penetrate tissue for several centimeters, photometric or spectroscopic methods can be used to measure the concentration of tissue metabolites such as hemoglobin by the measuring of the absorption of the light at one or more wavelengths. It is desirable and important that apparatus which measures the optical properties of tissues for clinical purposes provide quantitative information of a desired parameter, for example the concentration of oxyhemoglobin, or deoxyhemoglobin, glucose, or other metabolites.

In normal practice, the absolute determination of the concentration of a substance can be obtained by the measurement of the light transmitted through a sample of known thickness. Such a transmission measurement enables one to determine the absorption coefficient. Using this, the concentration of the measured substance can be calculated using the molar extinction coefficient of that substance via the Beer-Lambert law.

In the event of interference caused by more than one substance being present, measurement at different wavelengths can provide a method to determine the concentration of one or more different chemical species present, assuming that the materials present have different absorption spectra. The success of this method depends on the precision of the measurement and on the number of different substances present.

Additional problems arise in the photometry of tissues and other materials having high turbidity, such as emulsions. For purposes of this disclosure, it is to be understood that the term "tissue" includes living materials, but can also include non-living materials such as emulsions when it is desired to obtain similar data from such emulsions as is done by this invention with tissues. A measurement of the light transmitted through a slab of tissue has in the prior art been not practical, using non-invasive methods, except for special, thin regions of the body where light can shine entirely through the tissue and be detected on the other side. An example of this is a clinically used photometric blood oxygen sensor, which fits on the finger tip and shines directly therethrough to give real time oxygen concentration data.

In tissue photometry, the amount of transmitted light depends not only on the absorption of the medium being analyzed, but also on the scattering properties thereof. This light scattering greatly increases the complexity of photometric analysis of tissue, emulsions, and similar materials, since light scattering produces an unpredictable variation of the amount of light transmitted, which can vary significantly between various samples of tissues and the like.

Many different methods have been proposed to deal with this problem of scattering in photometric processes. For example, empirical corrections based on the type of tissue to be measured have been used to account for the effect of scattering on the absorption properties. For reflection measurements, theoretical models have been used to calculate the albedo of a surface. The success of all of these models has been poor, although there are commercially available instruments based upon those principles. A major problem is that in order to obtain a reasonable estimate of the concentration of a substance in tissue, some sort of a priori calibration must be performed, based on a statistical analysis of a large number of corresponding tissue samples. However, the range of variation of scattering within tissues from various individuals results in fundamentally unpredictable results, with the photometric results being strongly modified by factors such as skin color, and the amount of lipids in muscles.

The Hamamatsu Company of Japan in 1990 introduced a simple tissue spectrometer called NIRO 500 for the measurement of tissue oxygenation and total blood volume for neonatal monitoring. The principles of this device are as disclosed in Cope U.S. Pat. No. 5,032,024. The instrument is a steady state instrument, and is based on four different laser diodes emitting in the near infrared range. The light is brought to the tissue using a fiber optic system. The measurement is purely a steady-state one, with the optical path length in the tissue being not measurable. Thus, contrary to this invention, only relative quantities can be obtained, rather than absolute concentrations of oxy- and deoxyhemoglobin.

By this invention, absolute quantities of materials found admixed in highly turbid media may have their concentrations determined in a quantitative manner. Specifically, by this invention tissue metabolites may be quantitatively determined in real time, on a continuous basis, for example, concentrations of oxy- and deoxyhemoglobin, glucose, or the like. This can be accomplished without the need to pass light through a narrow portion of tissue, for example an extremity such as the finger. Rather, a sensor may be placed on a more central area of the body for determination of metabolite concentrations or other parameters there. This may be accomplished in a non-invasive manner, essentially instantaneously. Also, it may be possible for different metabolites present to be selectively and quantitatively determined on an essentially instantaneous basis.

DESCRIPTION OF THE INVENTION

In accordance with this invention, one may analyze for the presence and concentration of a substance in a highly turbid medium such as tissue of a patient by the steps of: sequentially illuminating and shutting off a plurality of light sources which are spaced at different distances from a light sensor, while modulating the intensity of light from said light sources at a first frequency and passing said modulated light through the turbid sample for testing and then to said sensor. One also provides a signal coherent with the modulated light, at a second frequency, to the light sensor, to modulate the gain of, or multiply the output of, the light sensor by the coherent signal, the second frequency being different from the first frequency. One then derives a resultant signal from the sensor while receiving the modulated light, the resultant signal being at a frequency of the difference between the first and second frequencies. From this, it becomes possible to detect at least two of the following characteristics of the modulated light sensed by the sensor; the phase shift component, the DC component, and the AC component.

The terms "DC component" and "AC component" define differing portions of the amplitude of the light from the light sources. Specifically, as previously described, the light from the light sources is of amplitude modulated intensity, so that it becomes brighter and dimmer in a cycle at the first frequency. This frequency is typically very high (e.g. 80 to 200 MHz) so that the fluctuation of light intensity is invisible to the eye. The AC component of the light comprises the change in light intensity from the peak of the cycle to the trough of the cycle; that is, the maximum change in the amplitude of the light intensity as it goes through its rapid cycle of amplitude modulation. The DC component is that portion of the light intensity measured from zero to the minimum intensity that the light always possesses, which of course is found at the bottom of the troughs of the wave pattern imposed on the light by the amplitude modulation.

Therefore, the maximum intensity of the light signal, found at the top of each wave, is the sum of the DC and AC light components. The minimum intensity of the light in its amplitude modulated cycle is the DC component alone.

In accordance with this invention, as the amplitude modulated light passes through human tissue or another highly turbid material to the sensor, the phase of the amplitude modulated light signal will shift, and the DC and AC components will attenuate. From this information, it is possible to obtain quantitative information as to the concentrations of certain materials present in the tissue on a real time or moment-by-moment basis.

This is preferably accomplished by sequentially turning on and off the plurality of light sources which are at differing distances from the light sensor. Thus, by the data provided from each of these plural light sources of differing distances, differing values for phase shift, DC component, and/or AC component may be determined separately for each light source to compute linear graphical data having characteristic slopes. Once the slopes are known, the values of scattering and absorption coefficients at the wavelength of the light used can be computed. From these values, particularly at two different wavelengths, absolute concentrations of materials present such as oxyhemoglobin, deoxyhemoglobin, and/or glucose can be calculated. Once the concentrations of oxyhemoglobin and deoxyhemoglobin are known, for example, the oxygen saturation and the blood volume of a patient can be calculated.

This can be accomplished in very short order through a microprocessor or the like, so that these values can be displayed in real time to a physician or nurse simply by applying a sensor head to the skin of a patient, without any need for the light to pass entirely through the tissue of the patient to the other side.

The sensor for detecting light in this invention can detect scattered light in the tissue, so that the light paths from the light sources to the sensor do not have to be linear. In fact, the direction of light emission and the general direction of light sensing may be parallel, as illustrated by the specific embodiment of the sensor head disclosed herein.

Preferably, the sensor for detecting light used herein may also carry the light sources in a common sensor head along with the sensor, plus a shield to prevent the direct access of light from the light sources to the light sensor without passing through the tissue of the patient.

The sensor instrument of this invention may carry an electronic processor for computing the slopes of at least two of the phase shift, the DC, and the AC components which are provided by separate signals from each of the plurality of light sources of differing distances. From this, the processor can also compute the scattering and absorption coefficients of the tissue. From this, for example, the absolute concentrations of at least one of oxyhemoglobin and deoxyhemoglobin present in the tissue may be computed from typically the absorption coefficient. The sensor instrument may then have means for displaying such concentration or concentrations as a real time value.

The intensity of the light from the light sources may preferably be amplitude modulated at about 50 to 150 MHz. The second frequency of the second signal is of the same order, but differing from the first frequency typically by about 10 Hz to 100 KHz.

Typically, the light which is used is of a wavelength of about 650 nm to about 1000 nm, with at least three light sources of differing distances being present. However, it is preferred for at least six light sources of differing distances to be present, with the light sources being disposed in a pair of rows to provide pairs of light sources in the respective rows of the same distance from the sensor. This permits the simultaneous gathering of data at different light wavelengths, which different light wavelengths are emitted each by one of the rows of the sensors.

It is also preferred for each of the plurality of light sources to be sequentially activated (illuminated) for a length of time that is an exact multiple of a wave having a frequency which comprises the difference between the first and second frequencies as described above (the "cross correlation frequency").

Also, the information sensed by the light source may be summed and averaged from about eight to about eight hundred times of repetition, to obtain an intensified average of the photometric information received from each light source.

Typically, the method and apparatus of this invention make use of principles of frequency domain fluorometry and/or phosphorimetry which are well known, being disclosed for example in Gratton U.S. Pat. No. 4,840,485, Gratton et al. U.S. Pat. No. 5,212,386, and Gratton et al. application Ser. No. 07/983,829, filed Dec. 1, 1992, among others.

DESCRIPTION OF SPECIFIC EMBODIMENTS

Figure 1:
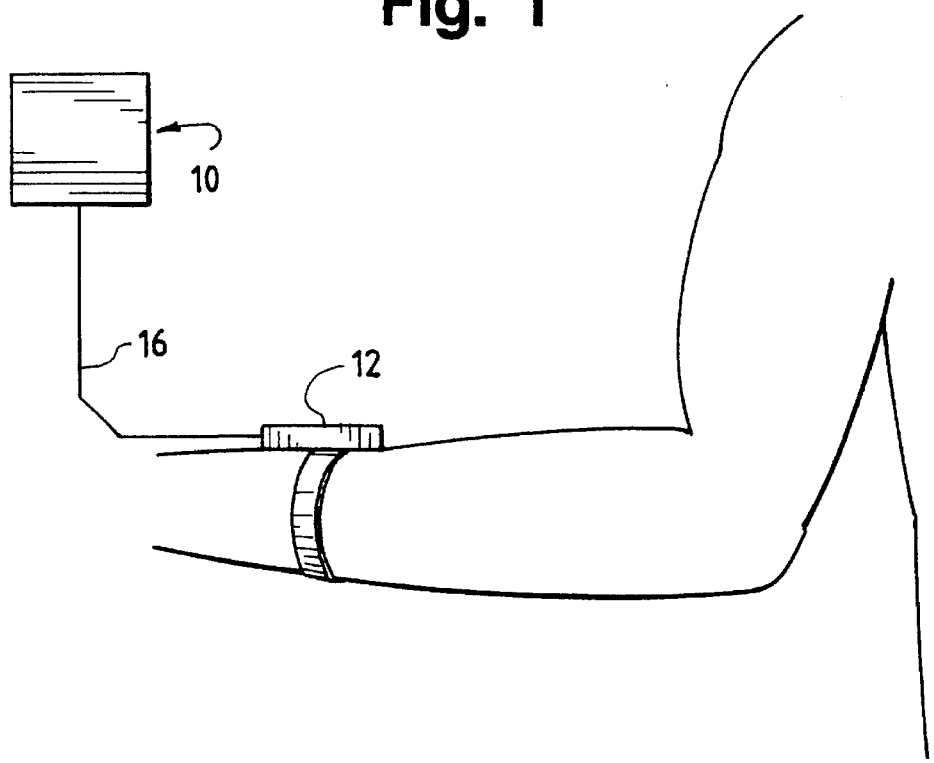
FIG. 1 is an elevational view of the sensor instrument of this invention, shown attached to the arm of a patient for sensing parameter of body tissue.
Figure 2:
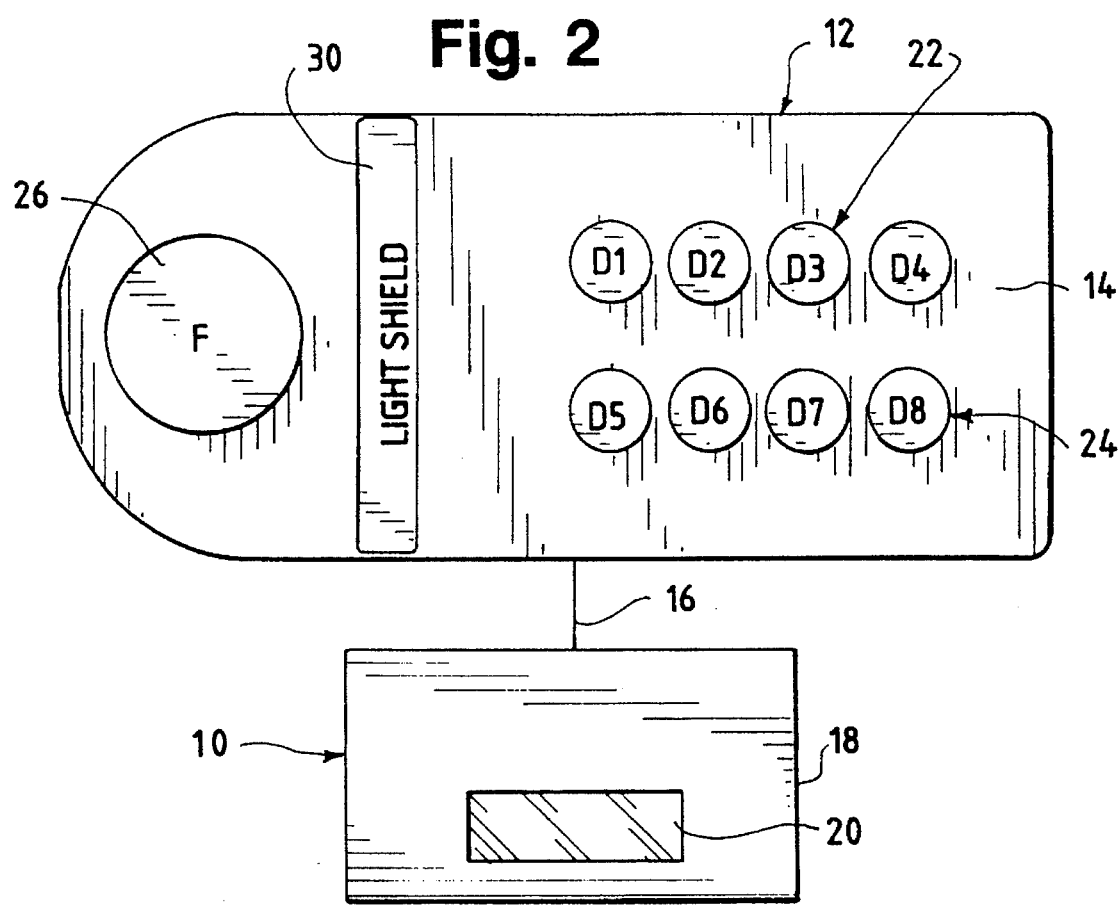
FIG. 2 is a schematic bottom plan view of the sensor instrument of FIG. 1, showing details of the sensor head.

In the drawings, a sensor instrument is shown for non-invasively and quantitatively determining the real time concentration of oxyhemoglobin and deoxyhemoglobin within living tissue of the patient. Sensor instrument 10 comprises a sensor head 12, which comprises a body having a sensor face 14 which may be flat or curved for better contact with the contour of a patient's arm, thigh, chest, or the like. Sensor 12 is placed with sensor face 14 in intimate contact with the skin of the patient. Cable 16 contains both an optical fiber and the electrical wires to convey both optical and electronic signals to processor unit 18. Alternatively, the light detector may be placed on the sensor head, and cable 16 is free of optical fibers. Data may be displayed at a readout window 20 in conventional manner.

Sensor head 12 carries eight light sources 22, 24 (individually labelled $D_1$–$D_8$) with four each of the respective light sources 22 and 24 being positioned in separate rows so that the respective light sources 22 and the respective light sources 24 are each at different distances from a conventional light sensor 26. Light sources 22, 24 may be light emitting diodes, laser diodes, or any other light source system which is capable of being amplitude modulated at the desired frequency range. Also, the wavelengths of the light sources are chosen to maximize the difference in light absorption in this specific embodiment of the oxyhemoglobin and deoxyhemoglobin species, specifically 700–900 nm.

Figure 4:
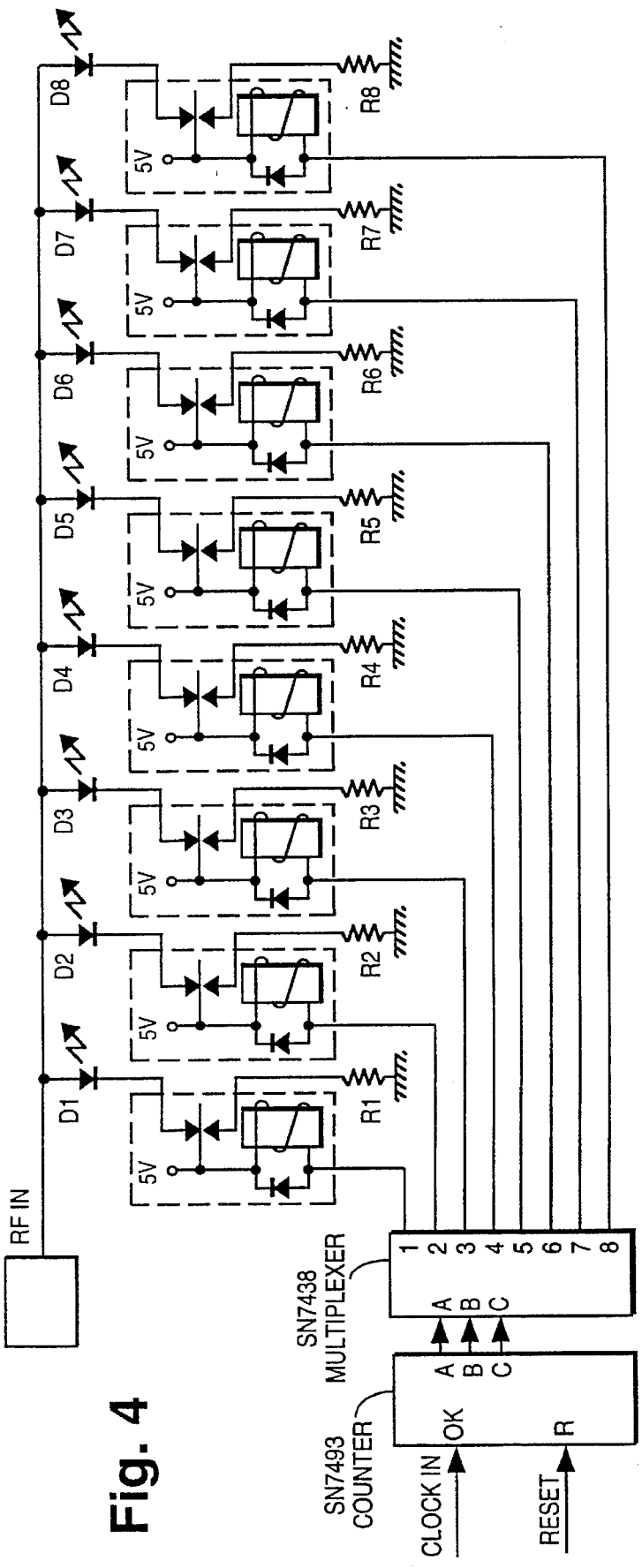
FIG. 4 is a diagram of a multiplexer circuit for turning the multiple light sources on and off in sequence, while causing the light emitted to be amplitude modulated at a high frequency.

By the multiplexer circuit of FIG. 4, the respective light sources 22, 24 are turned on and off, one at a time, in rapid succession. In this embodiment, the light sources are sinusoidally (amplitude) modulated at 120 MHz, to provide a frequency that maximizes the modulation of the source, and the sensitivity of the slopes described above to the scattering and absorption coefficients. Also, detectors or sensors 26 having good sensitivity at this frequency are readily available. Likewise, for hemoglobin detection, such a frequency provides a maximum signal-to-noise ratio.

Modulated light signals from the respective light sources 22, 24 enter the tissue of the patient, and travel in a highly scattered manner through the tissue of the patient to sensor 26. The direct transmission of light from each light source 22, 24 to sensor 26 without passing through tissue is prevented by a rubber light shield barrier 30, which projects slightly outwardly from face 14 of sensor head 12.

Figure 3:
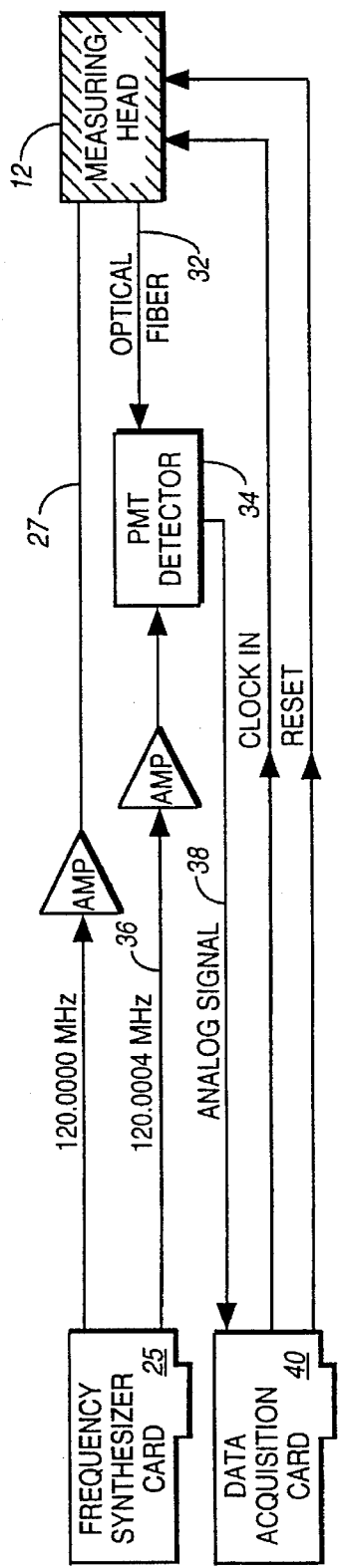
FIG. 3 is a block diagram of the electronics of the sensor instrument of the previous drawings.

The light passing through the tissue which is sensed by sensor 26 may be transmitted by an optical fiber 32 (FIG. 3), within connecting cable 16, which cable also carries wires, each communicating between sensor head 12 and processor unit 10. Light from optical fiber 32 passes to a photomultiplier detector 34.

Frequency synthesizer card 25 carries a frequency generator to provide an RF signal to head 12 and LEDs 22, 24 through wire 27 (also in cable 16), with conventional circuitry, to impose on the respective LEDs 22, 24 an amplitude modulation of 120.0000 MHz, which is the first frequency described above.

Frequency synthesizer card 25 also carries a frequency synthesizer which sends a second signal, coherent with the first but modulated at a second frequency, of 120.0004 MHz, through wire 36 to modulate the gain of photomultiplier detector 34. Thus, an analogue signal, which is a function of the signals through fiber 32 and wire 36, may be sent from detector 34 along wire 38 to data acquisition card 40. The particular analogue signal sensed by data acquisition card 40 may at be the "cross correlation frequency", which is the frequency of the difference between the first and second signals, or 400 Hz in this example. This well established method produces a beating of the 120 MHz modulated current in the detector photomultiplier with the 120.0004 MHz radio frequency signal injected at the photomultiplier dynode, the photomultiplier output through wire 38 being modulated at the 400 Hz cross-correlation frequency. The radio frequency harmonics may be rejected by a low pass filter at an amplifier in detector 34.

Thus, each light source 22, 24 may be turned on for a length of time that is an exact multiple of the 400 Hz cross-correlation frequency wave period, i.e. for a length of time which is 2.5 milliseconds or a multiple thereof. In a typical measurement, a minimum of 8 to about a maximum of 800 periods of the 400 Hz wave are collected, depending on the light intensity through the tissue obtained at sensor 26. Each of these measuring periods may be digitized sixteen times. All of the collected waves of a measuring period may be averaged together, giving an average wave comprising 16 points, similar to the process described in Gratton et al. U.S. Pat. No. 5,212,386. Then, the 16 point wave may be transformed using a fast Fourier transform algorithm to give the value of the phase shift (P) component, the direct current (DC) component, and/or the alternating current (AC) component of the fundamental harmonic frequency of 400 Hz.

The above process can be repeated for each of light sources 22 and 24. The respective light sources 22 may emit at one wavelength such as 720 nm, and the other light sources 24 may emit at another wavelength such as 850 nm, to obtain a double set of data. Each of the respective light sources 22 are at different distances from sensor 26, as are each of the light sources 24, so that the data of each of the individual light sources of each set will be different, the more distant light sources exhibiting greater light attenuation through the tissue. The result of this can be a set of four values of the DC, AC, and phase shift (P) components at each wavelength, dependent on known distances of the light sources from the sensor.

Signals from the light detector 34 received by the data acquisition card 40 are digitized by the card (ISS A2D card, for example). A computer calculates from these data the respective slopes (S) of at least two of the DC, AC, and P components provided by each of the sets of lights 22, 24, since each of the respective lights provides differing values for the DC, AC, and P components, coupled with a known, constant distance of each light source from sensor 26. This can be accomplished as follows:

Mathematical Background

In a frequency domain spectrometer the light intensity is sinusoidally modulated at a frequency f, generally in the 100 MHz region. The light source generated a photon density wave in the strongly scattering medium that propagates at a reduced velocity with respect to the velocity of light in water. This is due to the large number of collisions of the photons composing the photon density wave with the particles in the medium. At every point in space, the light intensity varies sinusoidally at the same frequency of the source, but it is phase shifted and attenuated with respect to the intensity of the source. The phase shift P and the attenuation of the sinusoidal modulated intensity AC and also of the average light intensity DC are a function of the distance from the source r and of the scattering ($\mu_s$) and absorption ($\mu_a$) coefficients, plus DC, AC and P values. The following relationship holds, when both light sources 22, 24 and detector 26 are placed on the surface of a large, uniform medium such as a patient's arm:

$$DC = \frac{DC_o e^{-r\sqrt{2s}}}{r^2}$$

$$AC = \frac{AC_o e^{-r\sqrt{s}\sqrt{x+1}}}{r^2}$$

$$P = P_o + r\sqrt{s}\sqrt{x-1}$$

where $$s = \frac{3}{2}\mu_a(\mu_a + \mu_s)$$

$$x = \sqrt{y^2 + 1}$$

$$y = \frac{2\pi f}{v\mu_a}$$

In the above set of equations, the distance r between source and detector can be accurately measured independently. The first frequency of light modulation f is also exactly known, and v is the velocity of light in water. The only unknown parameters are the scattering and absorption coefficients, and phase, DC and AC factors of the modulated light.

The above equations require that we determine separately the value of the phase, DC and AC factors of the light. Rather than determining these quantities independently, it may be more practical to measure the values of the DC, AC and P at several distances r. The slopes of the plots of $\ln(r^2 DC)$, $\ln(r^2 AC)$ and P as a function of r provide quantities that are independent from the source constants. It is from these slopes that the scattering and absorption coefficients are measured in this particular implementation of the frequency domain spectrometer. By a measurement of any two of the above quantities, i.e., DC and P, AC and P and DC and AC, we can determine the optical parameters of the medium if we first determine the slopes of the plots defined above. Let us indicate with $S_{dc}$, $S_{ac}$, and $S_p$ the three slopes previously defined. The equations that relate $\mu_a$ and $\mu_s$ to the above slopes can be obtained from the following formulas:

$$\mu_a = \frac{2\pi f}{v}(X^2 - 1)^{-1/2}$$

(used for determining concentrations)

$$\mu_s = \frac{S^2}{3\mu_a} - \mu_a$$

(which may be used to determine imaging properties, see U.S. Pat. No. 5,213,105.

Thus, the absorption and scattering coefficients can be measured independently.

The symbols X and S are defined as follows for the 3 different pairs of possible measurements.
Using AC and phase measurements $$X = \frac{S_{ac}^2 + S_p^2}{S_p^2 - S_{ac}^2}$$

$$S = \sqrt{S_{ac}^2 - S_p^2}$$

Using DC and phase measurements $$X = \frac{S_{dc}^2 + 2S_p^2}{S_{dc}^2}$$

$$S = S_{dc}$$

and using DC and AC measurements $$X = \frac{2S_{ac}^2 - S_{dc}^2}{S_{dc}^2}$$

$$S = S_{dc}$$

Thus, $\mu_a$ and $\mu_s$ can be calculated by the above equations.

As stated above, any two out of the three slopes, once calculated as above by data acquisition card 40, may be used to electronically compute by card 40 the values of the scattering and absorption coefficients at each of the wavelengths used respectively by the lights 22 and 24. Preferably, the phase shift (P) slope and the DC slope are the values used for computing the scattering and absorption coefficients. From these values, the absolute concentrations of oxyhemoglobin and deoxyhemoglobin can be calculated using the following relationships.

$$[O] = \frac{\mu_{a1}\epsilon_{d2} - \mu_{a2}\epsilon_{d1}}{\epsilon_{o1}\epsilon_{d2} - \epsilon_{o2}\epsilon_{d1}}$$

$$[D] = \frac{\mu_{a2}\epsilon_{o1} - \mu_{a1}\epsilon_{o2}}{\epsilon_{o1}\epsilon_{d2} - \epsilon_{o2}\epsilon_{d1}}$$

Where $\epsilon$ is the extinction coefficient, the subscript d1 represents the extinction coefficient of deoxyhemoglobin at the first wavelength (for example 720 nm); the subscript d2 represents the extinction coefficient of deoxyhemoglobin at the second wavelength (for example 850 nm). The subscript o1 represents the same coefficient for oxyhemoglobin at the first wavelength. The subscript o2 represents the same coefficient for oxyhemoglobin at the second wavelength.

Extinction coefficients for hemoglobin at various wavelenghts are available in the book by R. Lemberg and J. W. Legge entitled Hematin Compounds and Bile Pigments (Interscience, N.Y.) 1949. Specifically, the values for the various subscripts of epsilon are as follows: d1=921; d2=414; o1=230; o2=576, in units of $Mol^{-1}cm^{-1}$.

$\mu_{a1}$ and $\mu_{a2}$ are the respective absorption coefficients respectively at the first wavelength and the second wavelength for oxyhemoglobin and deoxyhemoglobin, dependent on the equation.

It can be seen that the above equations require the use of two different wavelengths of light, which can be emitted respectively from light sources 22 and light sources 24 as previously described.

From the above concentrations of the oxy and deoxy species, the oxygen saturation and the blood volume can be obtained using the following relationships.

Oxygen saturation of hemoglobin= 100%[O]/[O]+[D]);
Total hemoglobin=[O]+[D]

Figure 5:
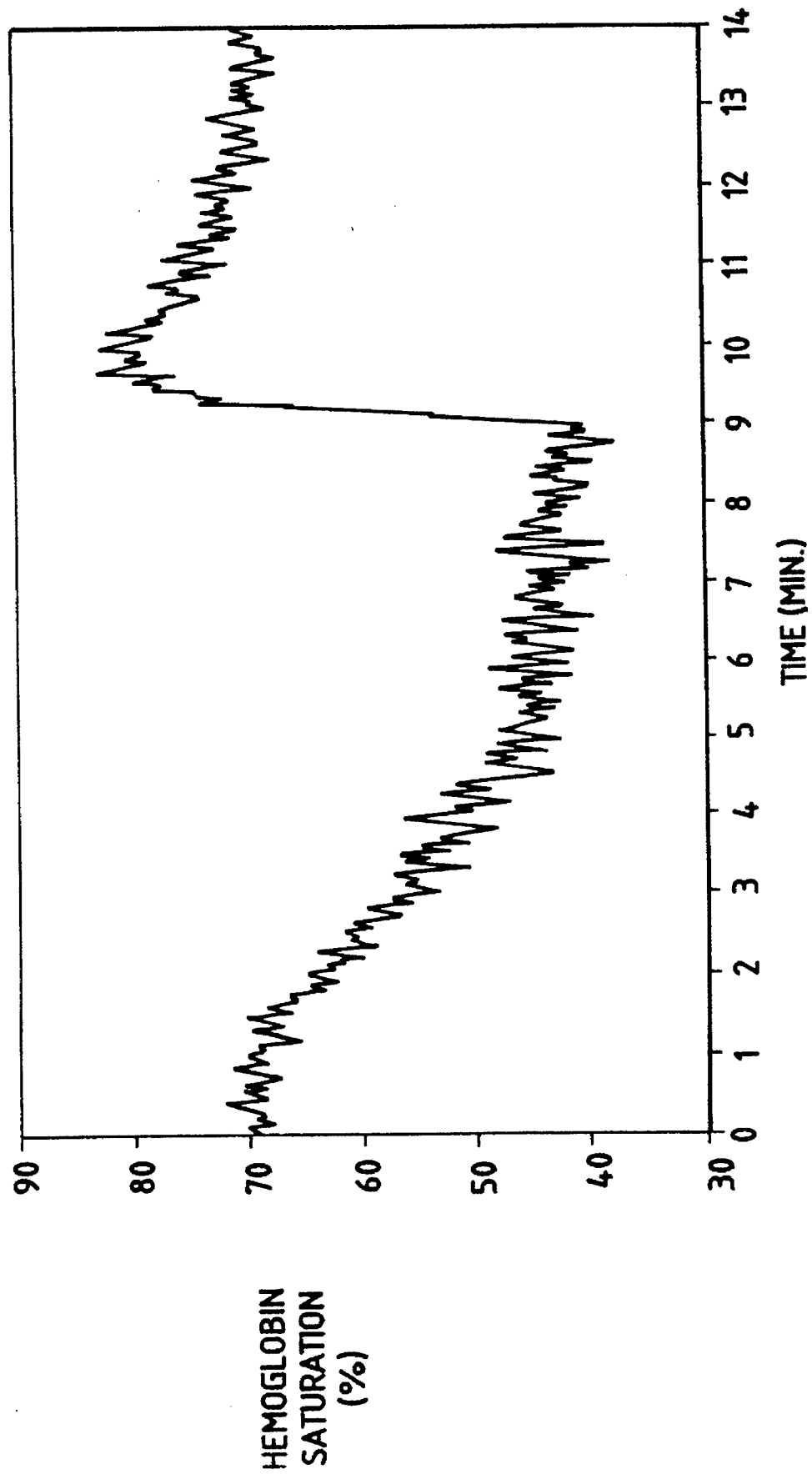
FIG. 5 is an exemplary graph showing how the apparatus of this invention is capable of determining hemoglobin saturation non-invasively in a patient in real time.

In this specific embodiment, accurate values of tissue oxygenation can be obtained in a fraction of a second. Thus, a record of hemoglobin saturation for an individual patient may be provided over time, as illustrated for example in FIG. 5, by the simple application of sensor head 12 to the skin of the patient.

It is not necessary to use all of the light sources 22, 24 in every procedure of the apparatus of this invention. More light sources, for example 16 or 32, may be used. Also, a multiplexing principle may be applied to a much larger number of light sources, if desired, for the simultaneous determination of the concentration of more metabolites, or other metabolites from data which is more difficult to acquire. If a fewer number of light sources are used than 4 or 8, the rate of data acquisition can be increased accordingly. A higher acquisition rate can allow the determination of signals correlated with heart and breathing rhythms.

If desired, a pair of detector heads may be provided to process signals from differing detectors or sensors 26 positioned at different locations on the body, or at different sampling rates, so that fast and slow processes can simultaneously be measured.

Cross correlation frequencies used herein may typically vary from about 40 Hz to about 4000 Hz with relatively comparable results. The use of higher values for a cross-correlation frequency allows better detection of faster processes.

While the light source multiplexer of FIG. 4 was constructed in this embodiment using mechanical relays, solid state switches may be used as a substitute if there is a desire to sequentially illuminate the respective lights 22, 24 at a rate faster than 2.5 milliseconds.

The respective light sources should be calibrated to give comparable light intensities at the detector 26. This may be done by the addition of series resistors to decrease the current in some of the light sources as needed. Light source equilibration permits the use of all the dynamic range of an analogue-to-digital converter, and may be done at the time of construction of the instrument.

However, it is desirable to periodically check the light source calibration for drifts over long use in the light source illumination characteristics. This calibration may be performed by placing head 12 on a solid block of a substance of known absorption and scattering coefficients, to determine the intensity of each light source as sensed by sensor 26. Note that this calibration procedure is different from the calibration of the present commercial oxymeters that need to be calibrated according to certain statistical tables based on the photometric characteristics of the particular tissue to be measured. The calibration that should be periodically accomplished in the instruments of this invention is a simple measurement of the light emission characteristics of the respective lights 22, 24, and nothing more.

The instrument of this invention permits direct, on screen, simultaneous monitoring in real time of several tissue parameters such as tissue oxygenation and total blood volume. Other physiologically important parameters such as blood flow and oxygen consumption can be computed as well from the independently determined concentration of oxyhemoglobin and deoxyhemoglobin, and the timed dependance of such parameters directly during a medical procedure, surgical operation, or the like.

The instrument described above in accordance with this invention utilizes the distance dependence of at least two out of three of the DC, AC, and phase shift values to calculate the scattering and absorption coefficients, preferably at two different wavelengths. The data obtained by this invention can also be used with different algorithms from that disclosed above to obtain desired information.

Both frequency synthesizer card 25 and data acquisition card 40 may basically be of the type described in the previously cited patents. Modifications of these cards for purposes of this invention may be readily accomplished by those skilled in the art.

The above has been offered for illustrative purposes only, and is not intended to limit the scope of the invention of this application, which is as defined in the claims below.

That which is claimed is:

1. A sensor instrument for use in measuring parameters of a highly scattering medium, which comprises:

a sensor head having a face for contact with the medium;

a sensor carried on said head for detecting light striking a portion of said face;

at least one group of light sources positioned to pass said light to said face through said medium, said light sources being of differing distances from said light sensor; and wherein all sources in each of said at least one group of sources emit light of substantially the same wavelength;

a timing circuit for causing sequential illumination and shutting off of said light sources;

a circuit for modulating an intensity of said light sources to provide amplitude modulated light signals at a first frequency;

circuitry for providing a second signal coherent with said amplitude modulated light signals, at a second frequency, to the light sensor;

circuitry for modulating the gain of, or for multiplying the output of, said light sensor by said second signal, said second frequency being different from said first frequency; and electronics for deriving a resultant signal from said light sensor while receiving said modulated light signals, said resultant signal being at a frequency of the difference between the first and second frequencies, and electronics to compute at least two of phase shift, DC, and AC components of said light signals which pass sequentially from said light sources through the medium to said light sensor.

2. The sensor instrument of claim 1 which further comprises a shield to prevent the direct access of light from said light sources to said light sensor without passing through said medium.

3. The sensor instrument of claim 1 in which a processor is provided for computing the slopes of at least two of said phase shift, DC, and AC components provided by signals from said at least one group of light sources of differing distances.

4. The sensor instrument of claim 3 in which said processor is also for computing at least one of a scattering and an absorption coefficient of the medium being measured from said slopes.

5. The sensor instrument of claim 4 in which said medium is tissue, and said processor computes absolute concentrations of at least one of oxyhemoglobin and deoxyhemoglobin present in said tissue, making use of a computed absorption coefficient, and means for display of said concentration as a real time value.

6. The sensor of claim 5, in which said at least one group of sources includes a first group that emit light of a first wavelength that is strongly absorbed by oxyhemoglobin and a second group of sources that emit light of a second, different wavelength, that is strongly absorbed by deoxyhemoglobin.

7. The sensor instrument of claim 1 in which the intensity of light from said light sources is amplitude modulated at 10–500 MHz, and the second frequency of the second signal differs from said first frequency by about 10 Hz–100 KHz.

8. The sensor of claim 1 in which one of said groups of light sources emits light having a wavelength of about 650 nm to about 1,000 nm.

9. The sensor of claim 1 in which at least three of said light sources of differing distances are present.

10. The sensor of claim 8 in which said at least one group of sources includes a first group of sources emitting light at a first wavelength and a second group of sources emitting light light at a second, different, wavelength, said groups of light sources together having at least six of said light sources, said light sources being disposed to provide pairs of light sources which are at the same distance from said sensor, to permit gathering of data at different light wavelengths.

11. The sensor instrument of claim 1 in which said electronics are also to compute at least one of a scattering coefficient and an absorption coefficient from said at least two of phase shift, DC, and AC components.

12. A sensor instrument for use in measuring parameters of body tissue, which comprises:

a sensor head having a face for contact with the skin of a patient;

a sensor carried on said head for detecting light striking a portion of said face;

light sources positioned to pass said light to said face through said tissue, said light sources being of differing distances from said light sensor, a first group of said light sources of differing distances emitting light of one frequency and a second group of said light sources of differing distances emitting light of another frequency;

a timing circuit for causing sequential illumination and shutting off of said light sources;

a circuit for modulating an intensity of said light sources to provide amplitude modulated light signals at a first frequency;

circuitry for providing a second signal coherent with said amplitude modulated light signals, at a second frequency, to the light sensor;

circuitry for modulating the gain of, or for multiplying the output of, the light sensor by said second signal, said second frequency being different from said first frequency:

electronics for deriving a resultant signal from said light sensor while receiving said modulated light signals, said resultant signal being at a frequency of the difference between the first and second frequencies; and a processor for receiving said resultant signal and determining at least two of phase shift, DC, and AC components of said light signals which pass sequentially from said light sources through the tissue to said light sensor, said processor also being for computing the slopes of said at least two of said phase shift, DC, and AC components provided by signals from said plurality of light sources of differing distances.

13. The sensor instrument of claim 12 in which said processor is capable of computing at least one of scattering and absorption coefficients of the tissue being measured from said slopes.

14. The sensor instrument of claim 13 in which said processor is capable of computing absolute concentrations of at least one of oxyhemoglobin and deoxyhemoglobin present in said tissue making use of said computed absorption coefficient, said sensor instrument having a display panel for displaying said concentration as a real time value.

15. The sensor instrument of claim 14, in which said first group of sources emit light of a wavelength that is strongly absorbed by oxyhemoglobin and said second group of sources emit light of a wavelength that is strongly absorbed by deoxyhemoglobin.

16. The sensor of claim 14 in which the intensity of light from said light sources is amplitude modulated at 10–500 MHz, and the second frequency of the second signal differs from said first frequency by about 10 Hz to 100 KHz.

17. The sensor instrument of claim 16 which further comprises a shield to prevent the direct access of light from said light sources to said light sensor without passing through said tissue.

18. The sensor instrument of claim 12 in which said processor is also for computing at least one of a scattering coefficient and an absorption coefficient from said slopes.

19. A sensor instrument for use in photometrically determining parameters of a highly scattering medium, which comprises:

a sensor head having a face for contact with said medium;

a sensor carried on said head for detecting light striking a portion of said face;

at least one group of light sources positioned to pass said light to said face through said medium, said light sources being of differing distances from said light sensor; and wherein all sources in each of said at least one group of sources emit light of substantially the same wavelength;

a timing circuit for causing sequential illumination and shutting off of said light sources;

a circuit for modulating an intensity of said illuminated light sources to provide amplitude modulated light signals at a first frequency;

electronics for providing frequency domain spectroscopy electronic processing of signals received by said sensor to provide a resultant signal which is a function of the modulated light signals received by said sensor; and a processor for receiving said resultant signal and determining at least two of phase shift, DC, and AC components of said light signals which pass sequentially from said light sources through said highly scattering media to said light sensor.

20. The sensor instrument of claim 19 in which said processor is capable of computing the slopes of at least two of said phase shift, DC, and AC components provided by light signals to said sensor from said plurality of light sources of differing distances.

21. The sensor instrument of claim 20 in which said at least one group of sources includes a first group of sources emitting light at a first wavelength and a second group of sources emitting light at a second, different, wavelength each group of said light sources emitting light at a different wavelength.

22. The sensor instrument of claim 20 in which said processor is also for determining at least one of a scattering coefficient and an absorption coefficient from said at least two of phase shift, DC, and AC components.

23. A sensor instrument for use in determining at least one of the scattering coefficient and absorption coefficient of a highly scattering medium, which comprises:

a sensor head having a face for contact with the medium;

a sensor carried on said head for detecting light striking a portion of said face;

at least one group of light sources positioned to pass light to said face through said medium, said light sources being of differing distances from said light sensor and wherein all sources in each of said at lest one group of sources emit light of substantially the same wavelength;

a timing circuit for causing sequential illumination and shutting off of said light sources; and electronics to compute at least two of phase shift, DC, and AC components of light from said light sources which has passed sequentially from said light sources through the medium to said light sensor, and to compute at least one of the scattering and absorption coefficients for said light sources.

24. The sensor instrument of claim 22 in which said medium is tissue and said electronics computes absolute concentrations of at least one of oxyhemoglobin and deoxyhemoglobin present in said tissue making use of said computed absorption coefficients and their slopes; and a readout display of said concentration as a real time value.

25. The sensor of claim 23 in which one of the groups of sources emits light having a wavelength from about 650 nm to about 1000 nm.

26. The sensor of claim 23, in which said at least one group of sources includes a first group that emit light of a first wavelength that is strongly absorbed by oxyhemoglobin and a second group of sources that emit light of a second, different wavelength, that is strongly absorbed by deoxyhemoglobin.

27. A sensor instrument for use in measuring parameters of a highly scattering medium, which comprises:

a sensor head having a face for contact with the medium;

a sensor carried on said head for detecting light striking a portion of said face:

at least one group of light sources positioned to pass said light to said face through said medium, said light sources being of differing distances from said light sensor, and wherein all sources in each of said at least one group of sources emit light of substantially the same wavelength;

a timing circuit for causing sequential illumination and shutting off of said light sources;

a circuit for modulating an intensity of said light sources to provide amplitude modulated light signals at a first frequency;

circuitry for providing a second signal coherent with said amplitude modulated light signals, at a second frequency, to the light sensor;

circuitry for modulating the gain of, or for multiplying the output of, said light sensor by said second signal, said second frequency being different from said first frequency; and electronics for deriving a resultant signal from said light sensor while receiving said modulated light signals, said resultant signal being at a frequency of the difference between the first and second frequencies, and electronics to compute at least two of phase shift, DC, and AC components of said resultant signals carrying information about the medium which is sequentially traversed through by the light signals emitted by said light sources, said electronics also being for computing at least one of a scattering coefficient and an absorption coefficient from said at least two of phase shift, DC, and AC components.

* * * * *